a12) United States Patent
Curro et al.

(10) Patent No.: US 6,830,800 B2
(45) Date of Patent: *Dec. 14, 2004

(54) ELASTIC LAMINATE WEB

(75) Inventors: John Joseph Curro, Cincinnati, OH (US); Douglas Herrin Benson, West Harrison, IN (US); Anthony Stephen Spencer, Hamilton, OH (US); John Brian Strube, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 45 days.

This patent is subject to a terminal disclaimer.

(21) Appl. No.: 09/886,730

(22) Filed: Jun. 21, 2001

(65) Prior Publication Data

US 2002/0016122 A1 Feb. 7, 2002

Related U.S. Application Data

(63) Continuation-in-part of application No. PCT/US00/34746, filed on Dec. 20, 2000, which is a continuation-in-part of application No. 09/584,676, filed on May 31, 2000, which is a continuation-in-part of application No. 09/467,938, filed on Dec. 21, 1999.

(51) Int. Cl.[7] .............................. B32B 3/02; B32B 3/10; B32B 5/26; B32B 27/12; D04H 1/00

(52) U.S. Cl. ........................ 428/136; 428/68; 428/72; 428/74; 428/131; 428/134; 428/137; 428/172; 428/196; 428/198; 442/328; 442/329; 442/392; 442/394; 442/399; 442/409

(58) Field of Search ...................... 239/34, 53, 55–57; 428/68–76, 131, 136, 137, 156, 172, 196, 198; 442/328, 329, 399, 394, 409, 392

(56) References Cited

U.S. PATENT DOCUMENTS

| 2,257,428 A | 9/1941 | Ruegenberg |
| 2,679,887 A | 6/1954 | Doyle et al. |
| 2,862,251 A | 12/1958 | Kalwaites |
| 2,896,692 A | 7/1959 | Villoresi |
| 3,081,500 A | 3/1963 | Griswold et al. |

(List continued on next page.)

FOREIGN PATENT DOCUMENTS

| EP | 0 112 654 A2 | 7/1984 |
| EP | 0 207 904 | * 1/1987 |
| EP | 0 127 483 B1 | 10/1989 |

(List continued on next page.)

OTHER PUBLICATIONS

U.S. Appl. No. 08/816,106, Curro et al., filed Mar. 14, 1997.
U.S. Appl. No. 09/027,039, McFall et al., filed Feb. 20, 1998.

(List continued on next page.)

*Primary Examiner*—Cheryl A. Juska
*Assistant Examiner*—Jenna-Leigh Befumo
(74) *Attorney, Agent, or Firm*—Angela Marie Stone; Roddy M. Bullock

(57) ABSTRACT

An elastic laminate web is disclosed. The elastic laminate web can be non-apertured or apertured, and comprises a first web, and a second web joined to the first web in a face to face relationship at a plurality of discrete bond sites having an aspect ratio of at least 2. The first and second webs form an interior region therebetween. An elastic material is disposed between the first and second webs. The elastic material is apertured in regions coincident the bond sites, such that the first and second webs are joined through the apertures. The laminate so produced can be stretched in a predetermined direction, such as by incremental stretching, to produce an apertured elastic laminate.

12 Claims, 10 Drawing Sheets

U.S. PATENT DOCUMENTS

| | | |
|---|---|---|
| 3,081,512 A | 3/1963 | Griswold |
| 3,354,022 A | 11/1967 | Dettre et al. |
| 3,485,706 A | 12/1969 | Evans |
| 3,542,634 A | 11/1970 | Such et al. |
| 3,574,109 A | 4/1971 | Yoshikawa |
| 3,597,299 A | 8/1971 | Thomas et al. |
| 3,681,182 A | 8/1972 | Kalwaites |
| 3,681,183 A | 8/1972 | Kalwaites |
| 3,695,967 A | 10/1972 | Ross |
| 3,695,985 A | 10/1972 | Brock et al. |
| 3,728,203 A | 4/1973 | Taylor |
| 3,800,364 A | 4/1974 | Kalwaites |
| 3,855,046 A | 12/1974 | Hansen et al. |
| 3,860,003 A | 1/1975 | Buell |
| 3,881,987 A | 5/1975 | Benz |
| 3,927,673 A | 12/1975 | Taylor |
| 3,929,135 A | 12/1975 | Thompson |
| 3,949,127 A | 4/1976 | Ostermeier et al. |
| 3,953,638 A | 4/1976 | Kemp |
| 4,062,993 A | 12/1977 | Seward |
| 4,101,625 A | 7/1978 | Haley |
| 4,116,892 A | 9/1978 | Schwarz |
| 4,135,021 A | 1/1979 | Patchell et al. |
| 4,153,664 A | 5/1979 | Sabee |
| 4,207,367 A | 6/1980 | Baker, Jr. |
| 4,223,059 A | 9/1980 | Schwarz |
| 4,276,336 A | 6/1981 | Sabee |
| 4,285,100 A | 8/1981 | Schwarz |
| 4,333,979 A | 6/1982 | Sciaraffa et al. |
| 4,342,314 A | 8/1982 | Radel et al. |
| 4,349,020 A | 9/1982 | Krikorian |
| 4,355,066 A | 10/1982 | Newman |
| 4,404,052 A | 9/1983 | Persson et al. |
| 4,414,970 A | 11/1983 | Berry |
| 4,418,123 A | 11/1983 | Bunnelle et al. |
| 4,421,812 A | 12/1983 | Plant |
| 4,522,863 A | 6/1985 | Keck et al. |
| 4,525,407 A | 6/1985 | Ness |
| 4,573,991 A | 3/1986 | Pieniak et al. |
| 4,588,630 A | 5/1986 | Shimalla |
| 4,600,620 A | 7/1986 | Lloyd et al. |
| 4,603,069 A | 7/1986 | Haq et al. |
| 4,606,964 A | 8/1986 | Wideman |
| 4,609,518 A | 9/1986 | Curro et al. |
| 4,629,643 A | 12/1986 | Curro et al. |
| 4,657,802 A | 4/1987 | Morman |
| 4,695,278 A | 9/1987 | Lawson |
| 4,720,415 A | 1/1988 | Vander Wielen et al. |
| 4,741,944 A | 5/1988 | Jackson et al. |
| 4,758,297 A | 7/1988 | Calligarich |
| 4,797,310 A | 1/1989 | Barby et al. |
| 4,801,482 A | 1/1989 | Goggans et al. |
| 4,808,178 A | 2/1989 | Aziz et al. |
| 4,816,025 A | 3/1989 | Foreman |
| 4,840,829 A | 6/1989 | Suzuki et al. |
| 4,847,134 A | 7/1989 | Fahrenkrug et al. |
| 4,891,258 A | 1/1990 | Fahrenkrug |
| 5,116,662 A | 5/1992 | Morman |
| 5,143,679 A | 9/1992 | Weber et al. |
| 5,151,092 A | 9/1992 | Buell et al. |
| 5,156,793 A | 10/1992 | Buell et al. |
| 5,167,897 A | 12/1992 | Weber et al. |
| 5,204,158 A | 4/1993 | Phillips et al. |
| 5,260,345 A | 11/1993 | DesMarais et al. |
| 5,268,224 A | 12/1993 | DesMarais et al. |
| 5,320,891 A | 6/1994 | Levy et al. |
| 5,338,766 A | 8/1994 | Phan et al. |
| 5,376,198 A | 12/1994 | Fahrenkrug et al. |
| 5,431,991 A | 7/1995 | Quantrille et al. |
| 5,451,219 A | 9/1995 | Suzuki et al. |
| 5,518,801 A | 5/1996 | Chappell et al. |
| 5,536,555 A | 7/1996 | Zelazoski et al. |
| 5,567,501 A | 10/1996 | Srinivasan et al. |
| 5,587,225 A | 12/1996 | Griesbach et al. |
| 5,595,567 A | 1/1997 | King et al. |
| 5,620,779 A | 4/1997 | Levy et al. |
| 5,623,888 A | 4/1997 | Zafiroglu |
| 5,626,571 A | 5/1997 | Young et al. |
| 5,628,097 A | 5/1997 | Benson et al. |
| 5,635,290 A | 6/1997 | Stopper et al. |
| 5,658,639 A | 8/1997 | Curro et al. |
| 5,662,634 A | 9/1997 | Yamamoto et al. |
| 5,681,302 A | 10/1997 | Melbye et al. |
| 5,683,374 A | 11/1997 | Yamamoto et al. |
| 5,683,794 A | 11/1997 | Wadsworth et al. |
| 5,691,035 A | 11/1997 | Chappell et al. |
| 5,714,107 A | 2/1998 | Levy et al. |
| 5,733,822 A | 3/1998 | Gessner et al. |
| 5,788,684 A * | 8/1998 | Abuto et al. ................ 604/368 |
| 5,804,021 A | 9/1998 | Abuto et al. |
| 5,830,555 A | 11/1998 | Srinivasan et al. |
| 5,846,232 A | 12/1998 | Serbiak et al. |
| 5,851,935 A | 12/1998 | Srinivasan et al. |
| 5,853,881 A | 12/1998 | Estey et al. |
| 5,891,544 A | 4/1999 | Chappell et al. |
| 5,906,879 A | 5/1999 | Huntoon et al. |
| 5,916,661 A | 6/1999 | Benson et al. |
| 5,919,411 A | 7/1999 | Rezai et al. |
| 6,015,605 A | 1/2000 | Tsujiyama et al. |
| 6,022,607 A | 2/2000 | James et al. |
| 6,025,050 A | 2/2000 | Srinivasan et al. |
| 6,027,593 A | 2/2000 | Lunt et al. |
| 6,054,202 A | 4/2000 | Takeuchi et al. |
| 6,057,024 A | 5/2000 | Mleziva et al. |
| 6,086,984 A | 7/2000 | DiMaggio, Jr. et al. |
| 6,106,925 A | 8/2000 | Palumbo |
| 6,203,654 B1 | 3/2001 | McFall et al. |

FOREIGN PATENT DOCUMENTS

| | | |
|---|---|---|
| EP | 0 164 740 B1 | 4/1990 |
| EP | 0 432 755 B1 | 5/1995 |
| EP | 0 432 763 B1 | 8/1995 |
| EP | 0 685 586 A2 | 12/1995 |
| EP | 0 687 757 A2 | 12/1995 |
| EP | 0 452 727 B1 | 3/1996 |
| EP | 0 758 543 A1 | 2/1997 |
| EP | 0 713 546 B1 | 3/1997 |
| EP | 0 677 284 B1 | 6/1999 |
| EP | 0 919 212 A2 | 6/1999 |
| EP | 0 945 251 A1 | 9/1999 |
| EP | 0 945 536 A2 | 9/1999 |
| EP | 0 955 159 A1 | 11/1999 |
| EP | 0 823 878 B1 | 8/2000 |
| JP | 08299385 A | 11/1996 |
| WO | WO 94/19179 A1 | 9/1994 |
| WO | WO 96/10979 A1 | 4/1996 |
| WO | WO 97/11662 A1 | 4/1997 |
| WO | WO 97/47264 A1 | 12/1997 |
| WO | WO 99/37476 A1 | 7/1999 |
| WO | WO 99/55273 A1 | 11/1999 |
| WO | WO 99/55532 A1 | 11/1999 |
| WO | WO 99/67081 | 12/1999 |
| WO | WO 00/76430 A1 | 12/2000 |
| WO | WO 01/45616 A1 | 6/2001 |

OTHER PUBLICATIONS

U.S. Appl. No. 09/886,740, Curro et al., filed Jun. 21, 2001.
U.S. Appl. No. 09/886,828, Curro et al., filed Jun. 21, 2001.
U.S. Appl. No. 09/886,894, Curro et al., filed Jun. 21, 2001.
U.S. Appl. No. 09/886,893, Curro et al., filed Jun. 21, 2001.
U.S. Appl. No. 09/886,831, Curro et al., filed Jun. 21, 2001.
U.S. Appl. No. 09/886,830, Curro et al., filed Jun. 21, 2001.
U.S. Appl. No. 09/886,829, Curro et al., filed Jun. 21, 2001.

* cited by examiner

ELASTIC LAMINATE WEB

CROSS REFERENCE TO RELATED APPLICATIONS

This application is: a continuation-in-part and claims priority of prior application PCT International Application Ser. No. US00/34746 (Case 7897R2) which designates the U.S., will publish in English, and was filed Dec. 20, 2000 in the names of Curro et al.; and a continuation-in-part and claims priority of prior application Ser. No. 09/584676 (Case 7897R2), filed May 31, 2000 in the names of Curro et al.; and a continuation-in-part and claims priority of prior application Ser. No. 09/467938 (Case 7897), filed Dec. 21, 1999 in the names of Curro et al.

FIELD OF THE INVENTION

This invention relates to an extensible multilayer laminate web, and more particularly to a laminate web wherein at least a elastic layer is extensible and apertured. In some embodiments the entire multilayer laminate web is extensible, elastic, and apertured.

BACKGROUND OF THE INVENTION

Laminate webs formed by the joining of discrete webs in a layered relationship are well known in the art. For example, laminate nonwoven webs are often utilized in disposable absorbent articles such as diapers and adult incontinence products. Such laminated webs can be used as a topsheet, backsheet, or side panels. One example of a laminate web is a film/nonwoven laminate useful as a backsheet of a disposable diaper. Nonwoven/nonwoven laminates are also utilized to provide additional bulk or softness to a web component. Likewise, film/film laminate webs can provide benefits by combining the characteristics of various films in a layered relationship. Laminate webs can also be called composite webs.

Often laminate webs are intended to combine properties of the constituent layers to achieve synergistic benefits. For example, elastic materials can be combined with nonwoven webs to form elastically extensible nonwoven webs. Such materials can exhibit a plurality of gathers, or rugosities, when in a relaxed state. Elastic composite webs are useful as elastic waist portions, or stretch ear portions of disposable absorbent articles.

For many applications of laminate webs, it is beneficial to have apertures therethrough. Apertures add texture, which contributes to utility as well as aesthetics. For example, as a cleaning wipe, a laminate with apertures can capture and hold dirt better than a wipe without apertures.

A beneficial method of aperturing a nonwoven web, including laminates of nonwoven webs is disclosed in EP-A-852,483, issued to Benson et al. Disclosed is a laminate material having, for example, at least one layer of a spunbonded web joined to at least one layer of a meltblown web, a bonded carded web, or other suitable material. Such apertured webs are useful as the topsheet in a disposable absorbent article. However, this disclosure does not teach laminating webs comprising elastomeric materials to make an elastically extensible apertured web.

A perforated multilayer elastic coversheet comprising an intermediate elastic layer between upper and lower nonwoven layers is disclosed in EP-A-784,461 issued to Palumbo. The upper and lower layers are connected to the intermediate layer only around the perimeters of the perforations. While providing an apertured, elastic laminate, it is not apparent that the method disclosed could produce elastic laminates economically. It is also not apparent that the elastic laminate would be elastically extensible in more than one direction.

Accordingly, it would be desirable to have an elastically extensible apertured nonwoven web, the apertured web being characterized by a plurality of openings, or perforations, in the web, and being elastically extensible in at least two directions.

Further, it would be desirable to have an economically attractive method for making an elastically extensible apertured nonwoven web.

BRIEF SUMMARY OF THE INVENTION

An elastic laminate web is disclosed. The elastic laminate web can be non-apertured or apertured, and comprises a first web, and a second web joined to the first web in a face to face relationship at a plurality of discrete bond sites having an aspect ratio of at least 2. The first and second webs form an interior region therebetween. An elastic material is disposed between the first and second webs. The elastic material is apertured in regions coincident the bond sites, such that the first and second webs are joined through the apertures. The laminate so produced can be stretched in a predetermined direction, such as by incremental stretching, to produce an apertured elastic laminate.

One method for forming the elastic laminate web of the present invention comprising the steps of:

(a) providing first and second web materials comprising thermoplastic material;

(b) providing at least one third elastomeric web material;

(c) providing a thermal point bonder having a plurality of protuberances;

(d) guiding the third elastomeric web material in a stretched condition between the first and second web materials in a face-to-face layered relationship to the thermal point bonder;

(e) displacing the third elastomeric web material with the protuberances at discrete, spaced apart locations to form apertures in the third material; and (f) thermally point bonding the first and second outer web materials to form bond sites at discrete, spaced apart locations coincident with the protuberances, thereby forming a bonded laminate.

To make an apertured elastic web, the method comprises the additional step of:

(g) stretching the bonded laminate to form apertures in the elastomeric laminate web.

(h)

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

Figure 1:
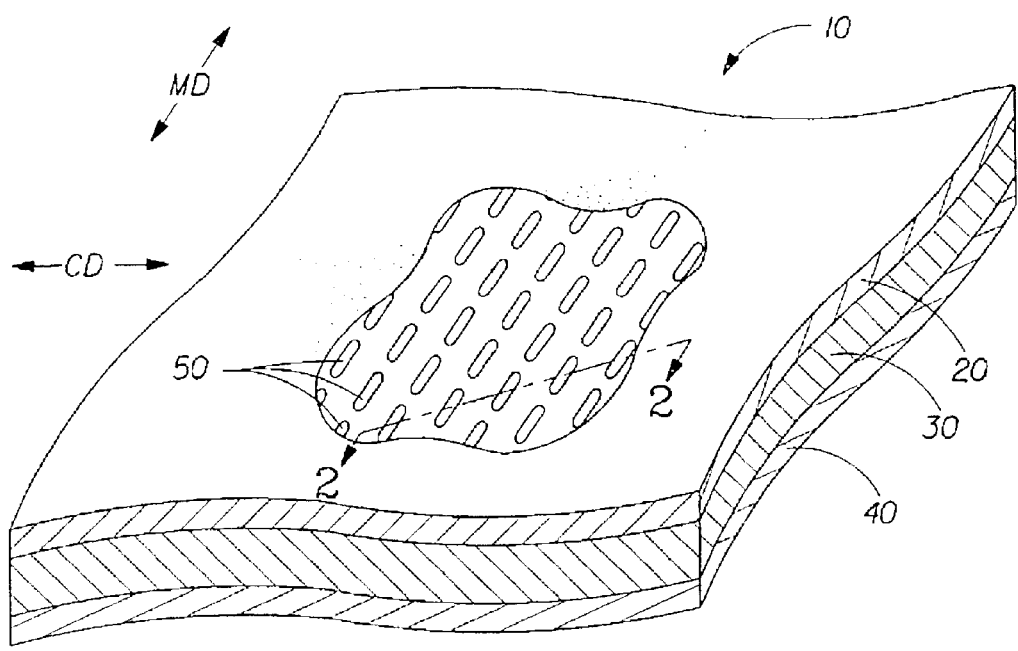
FIG. 1 is a perspective of one embodiment of a laminate web of the present invention.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

As used herein, the term "nonwoven web" is used in its plain meaning as understood in the art and refers to a web that has a structure of individual fibers or threads which are interlaid, but not in any regular, repeating manner. Nonwoven webs have been, in the past, formed by a variety of processes, such as, for example, meltblowing processes, spunbonding processes and bonded carded web processes.

As used herein, the term "microfibers", refers to small diameter fibers having an average diameter not greater than about 100 microns.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "spunbonded fibers", refers to small diameter fibers which are formed by extruding a molten thermoplastic material as filaments from a plurality of fine, usually circular, capillaries of a spinneret with the diameter of the extruded filaments then being rapidly reduced by drawing.

As used herein, the term "unitary web" refers to a layered web comprising two or more webs of material, including nonwoven webs, that are sufficiently joined, such as by thermal bonding means, to be handled, processed, or otherwise utilized, as a single web.

As used herein, "laminate" and "composite" when used to describe webs of the present invention, are synonymous. Both refer to a web structure comprising at least two webs joined in a face to face relationship to form a multiple-layer unitary web.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiaotactic and random symmetries.

As used herein, the term "elastic" refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches.

Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force. Such materials are denoted herein by the term "highly elastic" which refers to any material which upon application of a biasing force, is stretchable, that is, elongatable, at least about 200 percent (i.e., to a stretched, biased length, which is at least about 300 percent of its relaxed unbiased length), and which, will to within 105 percent of their initial relaxed length, upon release of the stretch force. Therefore, highly elastic materials are generally also elastic, but not all elastic materials are highly elastic.

As used herein, the term "nonelastic" refers to any material that does not fall within the definition of "elastic" above.

As used herein, the term "extensible" refers to any material which, upon application of a biasing force, is elongatable, at least about 25 percent without experiencing catastrophic failure. Catastrophic failure includes substantial tearing, fracturing, rupturing, or other failure in tension such that, if tested in a standard tensile tester, the failure would result in a sudden significant reduction in tensile force. As used herein, the term "highly extensible" refers to any material which, upon application of a biasing force, is elongatable, at least about 100 percent without experiencing catastrophic failure.

The Laminate Web

The laminate web 10 of the present invention comprises at least three layers or plies, disposed in a layered, face-to-face relationship, as shown in FIG. 1. The layers should be sufficiently thin to be processible as described herein, but no actual thickness (i.e., caliper) is considered limiting. A first outer layer 20, is preferably thermally bondable, and is preferably a nonwoven web comprising a sufficient quantity of thermoplastic material, the web having a predetermined extensibility and elongation to break. By "sufficient quantity" is meant a quantity of thermoplastic material adequate to enable enough thermal bonding upon application of heat and/or pressure to produce a unitary web. A second outer layer, 40, is preferably the same material as first outer layer 20, but may be a different material, also being thermally bondable and having a predetermined extensibility and elongation to break. At least one elastomeric elastic layer 30 is disposed between the two outer layers. The laminate web 10 is processed by joining means, such as by ultrasonic welding, or thermal calendaring as described below to provide a plurality of melt bond sites 50 that serve to couple the outer layers 20 and 40, and, in some embodiments, portions of elastic layer 30, thereby forming the constituent layers into a unitary web. When joined together, the two outer layers form an interior region between them. The interior region is the space between the outer layers surrounding the bond sites 50. In a preferred embodiment, the elastic layer 30 substantially fills the interior region, the elastic layer 30 being apertured coincident the bond sites 50.

While the laminate web 10 is disclosed primarily in the context of nonwoven webs and composites, in principle outer layers 20 and 40 of the laminate web 10 can be made out of any web materials that meet the requirements, (e.g., melt properties, extensibility) as disclosed herein. For example, the outer layers 20 and 40 can be thermoplastic films, micro-porous films, apertured films, a woven fabric, and the like. In general, it is required that outer layer materials be flexible enough to be processed as described herein.

Non-Apertured Embodiment

Figure 2:
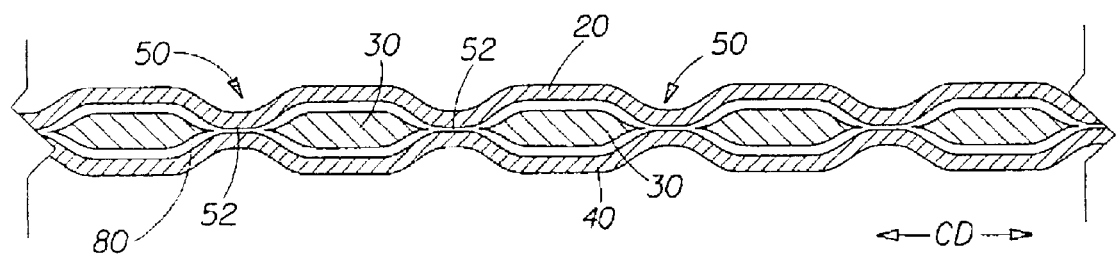
FIG. 2 is a cross-sectional view of a portion of the laminate web shown in FIG. 1.

In one embodiment, as shown in cross-section in FIG. 2, elastic layer 30 can be apertured, without aperturing the two outer layers to provide a three-layer laminate characterized by the laminate web 10 (as a whole) being un-apertured, while the elastic layer 30 is apertured. Importantly, the web of the present invention can be made by the method of the present invention without requiring registration of the layers to ensure bonding of the outer layers through the apertures of the elastic layer(s). One way of describing a preferred embodiment of a web 10 as described above, is that the unitary web 10, when viewed orthogonally by the un-aided human eye from a distance of approximately 50 cm, exhibits no apertures or perforations through the entire laminate, but bond sites 50 are nevertheless visible.

The laminate web 10 is further characterized in that the joining of the three plies into a unitary web can be achieved in the absence of adhesive. That is, in certain preferred embodiments no adhesive is required to bond the plies together; joining is achieved by the input of energy into the constituent layers, such as by thermal melt bonding of the two outer layers together at the melt bond sites 50. In other embodiments, the energy input can be via ultrasonic bonding. Accordingly, a significant benefit of the present invention is the provision of an elastic laminate web, that is a unitary web formed without the use of adhesives. Not only does this simplify processing and lower the cost of the elastic laminate web, when certain materials such as nonwoven webs are used, it results in a more flexible, softer web.

As shown in FIG. 2, elastic layer 30 is chosen such that when the constituent web layers of laminate web 10 are processed by the method of the present invention, portions of elastic layer 30 in the region of the melt bond sites 50 separate to permit the first outer layer 20 to melt bond directly to the second outer layer 40 at the interface of the two materials 52 at melt bond sites 50. Thus, apertures in the elastic layer 30 are formed in the lamination step by displacement, just prior to the bonding of the outer layers as detailed by the method of the present invention below. In this manner, elastic layer 30 can be provided as an unapertured web, avoiding complex registration steps to align apertures in registry with bond sites when laminated. Further, elastic layer 30 need not be thermally compatible with outer layers 20 and 40. Elastic layer 30 need not be a thermoplastic material, and need not even have a melting point. It simply needs to be displaceable by the forces exerted by the processing equipment as detailed below. The elastic layer can be a thermoset material with no melting point. If it has a melting point, it is preferably at least about 10 degrees Centigrade higher, more preferably about 20 degrees Centigrade higher than either outer layer.

Another advantage of the method of the present invention is that, in some embodiments, e.g., for solid core elastic layer 30 materials (i.e., a continuous sheet, that is, not having substantial apertures, gaps, or other voids), it results in a unitary web having an apertured elastic layer 30 in full, intimate contact with the outer layers 20, and 40. By "full" and "intimate" is meant that elastic layer 30 fills all the unbonded regions between outer layers 20 and 40 such that outer layers 20 and 40 do not contact except at the bond sites 50. Of course, it is recognized that some elastic materials of interest have significant air content (e.g., elastic nonwoven materials), and filling "all" the unbonded region between outer layers 20 and 40 is not meant to imply that all air content is removed.

The elastic layer 30 can be stretched in at least one direction before outer layers 20 and 40 are bonded to one another, i.e., either in the MD or CD direction. For example, as shown below with reference to the method for making, elastic layer 30 can be stretched in the machine direction MD prior to the laminate web being bonded into a unitary web. In this manner, an elastic composite is produced. Once the tension is removed from the elastic layer 30 it can freely retract to an untensioned state, and the two outer layers 20 and 40 become gathered, giving good three-dimensional puckering in a direction generally orthogonal to the direction of extension.

Elastic layer 30 can be involved, or participate, in the bonding between outer layers 20 and 40. By "involved" is meant that the elastic layer can, to some extent, be in intimate contact with, and possibly partially merged with, one or both immediate outer layers. The involvement may be due to actual melt bonding about the perimeter of bond site 50 (e.g., for thermoplastic elastic layers 30), or it may be due to mechanical interaction, such as by entanglement (e.g., for a fibrous elastic layer 30 between fibrous nonwoven layers), also about the perimeter of bond site 50.

Without being bound by theory, it is believed that the process of the present invention facilitates such separation of elastic layer 30 by shearing, cutting, or otherwise fracturing the elastic layer 30, and displacing the material of the elastic layer 30 sufficiently to permit thermal bonding of the two outer layers 20 and 40. Thus, elastic layer 30 must be chosen to have properties that permit such displacement. Importantly, it is not required that the elastic layer 30 be melted out of the region of the thermal bond sites. Elastic layer can be elastic or highly elastic depending on the desired end results and purposes of the resulting unitary web.

Figure 3:
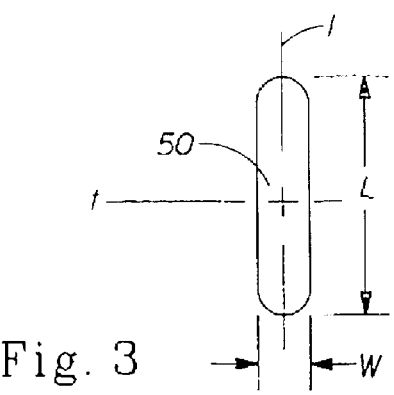
FIG. 3 is a magnified detail view of one bond site of a laminate web of the present invention.

Without being bound by theory, it is believed that to accomplish the displacement of elastic layer 30 to form apertures therein and to bond the outer layers, the thermal point calendaring described below should form thermal bond sites having a narrow width W dimension and a high aspect ratio. For example, FIG. 3 shows the melt area of a single melt bond site 50 having a narrow width dimension W and a high aspect ratio, i.e., the length, L, is much greater than the width, W. The length L should be selected to permit adequate bond area while width W is sufficiently narrow such that the protuberance used to form the bond site (as described below) can cut, shear, displace, or otherwise pierce the elastic layer 30 at the region of the bond sites by the method described below. Width W can be between about 0.003 inches and 0.020 inches, but in a preferred embodiment, is between about 0.005 inches and 0.010 inches, and may be adjusted depending on the properties of elastic layer 30.

It is believed that the aspect ratio of melt bond site 50 can be as low as about 2 (i.e., ratio of L/W equals 2/1). It can also be between about 3 and 100 or between about 3 and 50 or preferably between about 4 and 30. In one preferred embodiment, the aspect ratio was about 10 and in other embodiment about 25. It is believed that the aspect ratio of the melt bond sites 50 is limited only by the corresponding aspect ratio of the point bonding protuberances of the calendaring roller(s), as detailed below.

In a preferred embodiment, the longitudinal axis of each bond site, 1, which corresponds directionally to the length dimension of bond site 50, is disposed in a regular, repeating pattern oriented generally parallel to the machine direction, MD as shown in FIG. 1. But the longitudinal axis of each bond site may be disposed in a regular, repeating pattern oriented in the cross machine direction, or randomly oriented in a mixture of cross and machine directions. For example, the bond sites 50 can be disposed in a "herringbone" pattern.

When nonwoven webs are used as constituent layers of laminate 10, an important distinction should be drawn between bond sites 50 which bond together outer layers 20 and 40 by the method of the present invention, and thermal bond sites that may be present in the constituent layers themselves. For example, nonwoven webs are typically consolidated by thermal bonding in a regular pattern of discrete spaced apart fused bonding areas, such as the pattern disclosed in U.S. Pat. No. 3,855,046 to Hansen et al., and the patterns shown generally in FIGS. 10 and 11 of U.S. Pat. No. 5,620,779 to Levy et al. Other films, nonwoven webs, and the like may have thermal embossments for aesthetic reasons. Therefore, as shown in FIG. 18, in the unitary web 10 there may be many thermal bond sites, some of which are bond sites 50, and others which are bond sites in the base nonwoven (diamond shaped sites), for example.

The bond sites of the base nonwoven do not typically have an aspect ratio greater than about 1, so that these bonds do not typically form apertures in the constituent layer during the stretching step disclosed below. Also, the spacing of such bond sites is typically a repeating pattern of bonded and unbonded area which may or may not provide for machine direction (MD) columns of bonded area next to columns of unbonded area. After forming bond sites 50, however, there is not likely to be any significant MD columns of unbonded areas; the overall bond pattern of any constituent nonwoven fabric is a combination of existing bonded areas and bond sites 50. As shown in FIG. 18, together the two sets of bond sites result in a complex pattern of bond sites that may or may not be described as columnar, regular, or uniform.

The resulting web of the present invention, as shown in cross-section in FIG. 2, is a laminate web 10 that is itself unapertured, but the elastic layer 30 is apertured coincident the regions of the bond sites 50. As stated above, by "unapertured" is meant that, on the whole, the laminate web 10 is considered unapertured. It is recognized that the unapertured laminate web 10 of the present invention may have localized cut through, or tearing at bond sites 50 due to materials and processing variability or post lamination handling. Ideally, such cut through of the entire web is minimized and eliminated. Likewise, it is recognized that in some instances, there may not be complete displacement of the elastic layer 30 at all locations of bond sites 50 such that some localized portions of elastic layer 30 may not be apertured (and the outer layers not bonded). Nevertheless, the description herein is made for the laminate web 50 as a whole, and is not meant to be limited by aberrations or anomalies due to potential material or processing variables.

To produce the webs of the present invention, including as described with reference to FIG. 2, the outer layers should have sufficient elongation to permit the necessary local deformation in the immediate vicinity of bond sites 50. Thus, the outer layers 20 and 40 can be extensible, highly extensible, elastic, or highly elastic.

The elastic layer 30 itself need not be thermally compatible with the outer layers. The elastic layer 30 need not even be melt processible. It can be, for example, a thermoset material, such as a polyester elastomeric film, such as elastomeric Hytrel® from DuPont. The elastic layer 30 can be another nonwoven having suitable properties for processing into an apertured layer. If elastic layer 30 has a melting point, it is preferably at least about 10 degrees Centigrade higher, more preferably about 20 degrees Centigrade higher than the outer layers. However, elastic layer 30 need not have a melting point, and may simply experience softening at the calendaring temperatures required to bond the laminate.

A further benefit of the present invention is the capability to combine both thermoplastic and non-thermoplastic materials without any adhesives, to provide fabric-like composites having elastomeric properties. For example, many elastic materials, including elastomeric films or similar materials are not soft and clothlike, but have the look and feel of a plastic film, often a tacky film. When used in a laminate web 10 of the present invention, for example with nonwoven outer layers, the elastic laminate web can exhibit the softness of a nonwoven with the elasticity of an elastomer. Again, this laminate can be, and is preferably, made without the use of adhesives to bind the web into a unitary web.

Apertured Embodiments

A further benefit of the present invention is obtained when the non-apertured thermally bonded laminate web described above is stretched or extended in a direction generally orthogonal to the longitudinal axis, 1, of melt bond sites 50. The melt bonding at the melt bond sites 50 tends to make localized weakened portions of the web at the bond sites. Thus, as portions of the web 10 are extended in a direction generally orthogonal to the longitudinal axis 1 of bond sites 50 (i.e., in the CD direction as shown in FIG. 1), the material at the bond site fails in tension and an aperture is formed. The relatively high aspect ratio of melt bond sites 50, permits a relatively large aperture to be formed upon sufficient extension. When the laminate web 10 is uniformly tensioned, the result is a regular pattern of a plurality of apertures 60 corresponding to the pattern of melt bond sites 50.

Figure 4:
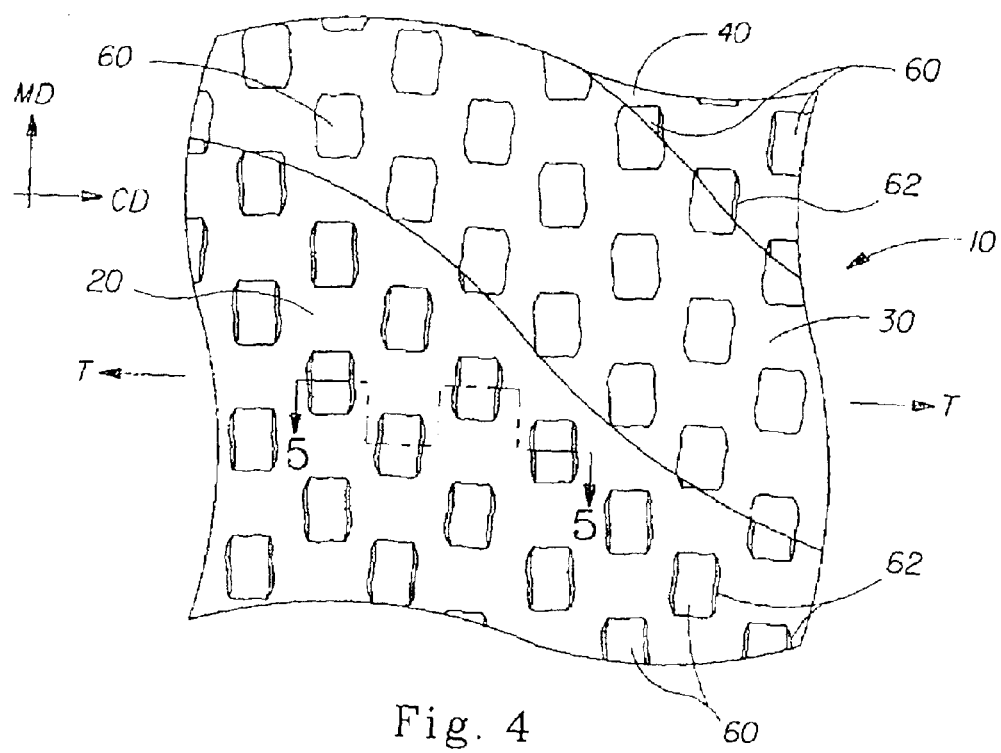
FIG. 4 is a top plan view of another embodiment of the laminate web of the present invention.

FIG. 4 shows a partially cut-away representation of an apertured laminate of the present invention. As shown, the partial cut-away permits each layer or ply to be viewed in a plan view. The laminate web 10 shown in FIG. 4 is produced after the thermally bonded laminate is stretched in a direction orthogonal to the longitudinal axis of the melt bond sites, in this case, in the cross-machine direction, CD with sufficient elongation in the direction of extension to cause apertures to form. As shown, where formerly were melt bond sites 50, apertures 60 are produced as the relatively weak bond sites fail in tension. Also as shown, elastic layer 30 can remain generally uniformly distributed within laminate 10, depending on the material properties of elastic layer 30.

When apertures 60 are formed, the thermally bonded portions of outer layers 20 and 40 remain primarily on the portions of the aperture perimeters corresponding to the length dimension of bond sites 50. Therefore, each aperture 60 does not have a perimeter of thermally bonded material, but only portions remain bonded, represented as 62 in FIG. 4.

To the extent that elastic layer 30 is involved, or participates, in any bonding between outer layers 20 and 40, it also participates in the remnant of bonded portions 62, as shown in FIG. 4. The involvement may be due to some degree of actual melt bonding about the perimeter of bond site 50 (e.g., for thermoplastic elastic layers 30), or it may be due to mechanical interaction, such as by entanglement (e.g., for fibrous elastic layer 30 between fibrous nonwoven layers).

Figure 5:
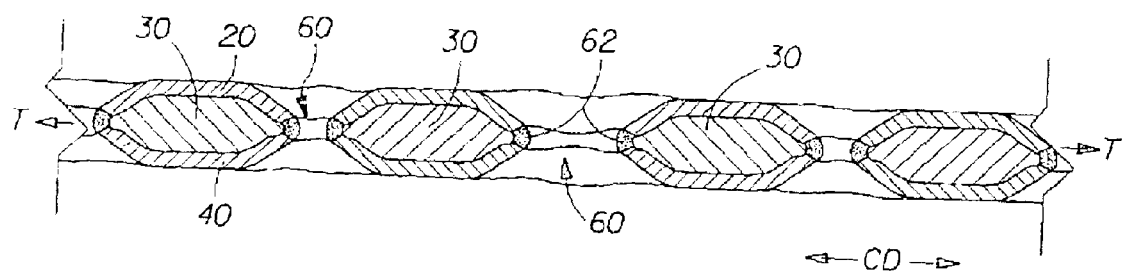
FIG. 5 is a cross-sectional view of a portion of the laminate web shown in FIG. 4.
Figure 6:
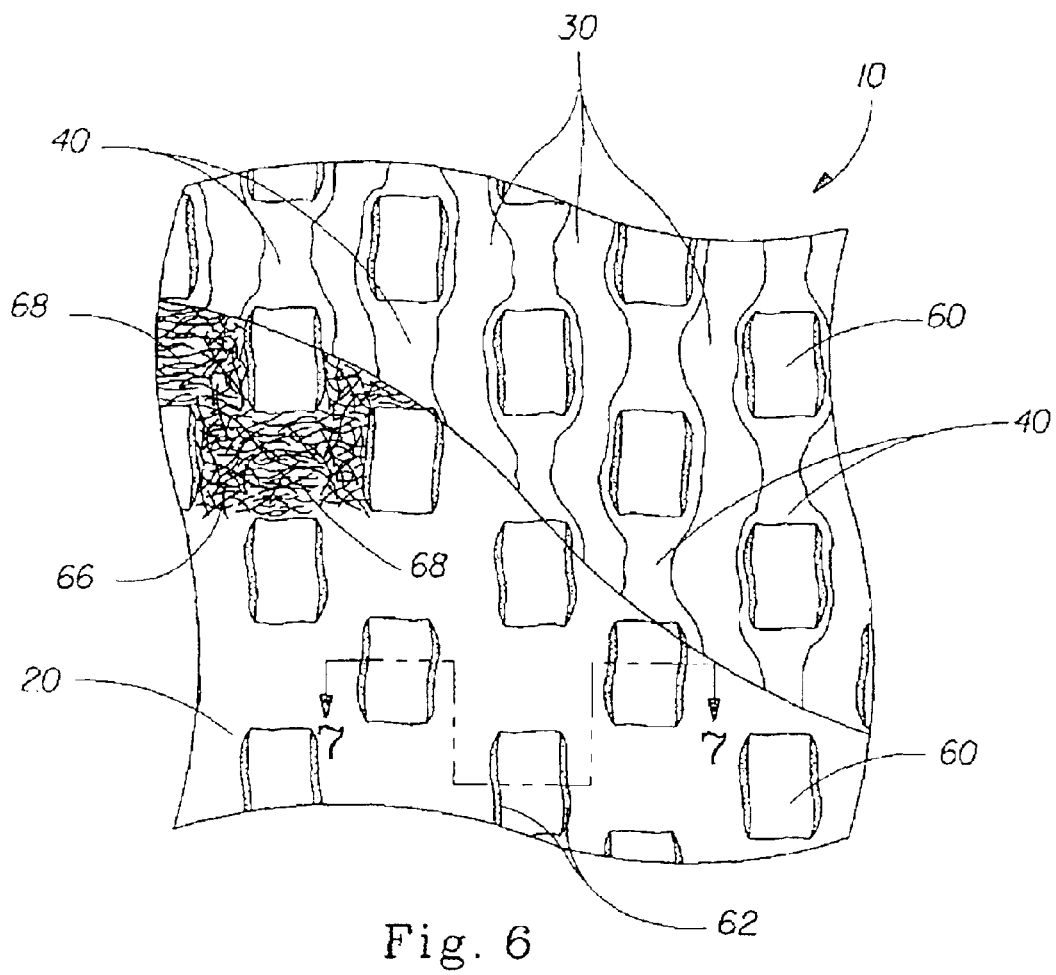
FIG. 6 is a top plan view of another embodiment of the laminate web of the present invention.
Figure 7:
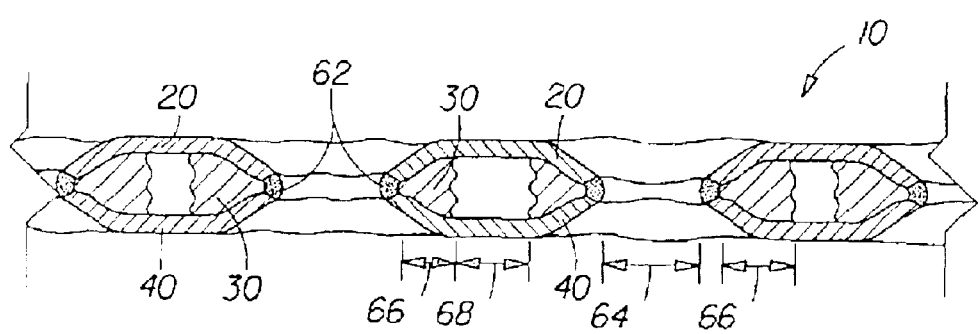
FIG. 7 is a cross-sectional view of a portion of the laminate web shown in FIG. 6.
Figure 8:
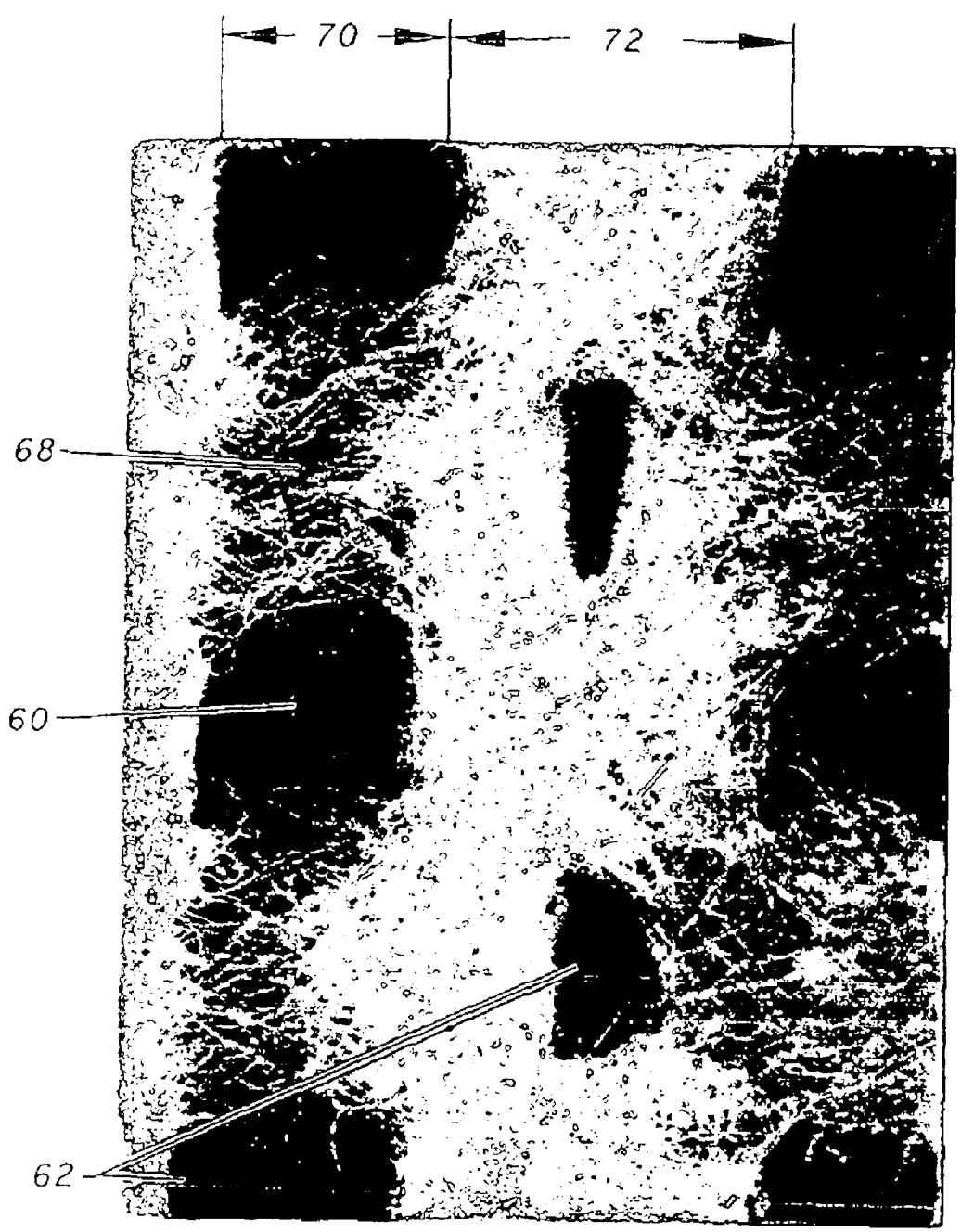
FIG. 8 is a photomicrograph of one embodiment of a laminate web of the present invention.

FIG. 5 is a schematic representation of the cross-section denoted in FIG. 4. As shown, apertures 60 form when the laminate web is elongated in the direction T.

Another benefit of the present invention is obtained when the laminate is extended as described with reference to FIG. 4, but the elastic layer 30 provides a restoration force to cause a retraction of the laminate web in the cross machine direction. Thus, in this embodiment, when the elastic layer 30 is pre-tensioned as described above, and incrementally stretched in a direction generally orthogonal to the direction of pre-tension, a bi-directional stretch laminate is produced. For most elastomeric materials, the resulting laminate is effectively a multi-directional stretch laminate.

In another method, one or both webs 120 or 140 could be incrementally stretched and consolidated by stretching, to provide precursor webs that have cross direction stretch potential "built in" prior to being bonded at the thermal point bond roller arrangement 108 as shown above. Incremental stretching precursor webs 120 or 140 could can be accomplished by processing the webs through an incremental stretching system 132 as discussed above. Consolidation can be achieved by means known in the art, including stretching in the machine direction, which yields a corresponding narrowing of the width in the cross direction.

Another embodiment of a laminate web of the present invention utilizing nonwoven webs as the outer layers is characterized by distinct regions differentiated by fiber orientation. Differential fiber orientation can be achieved by providing for localized regions within the web that experience greater extension than other regions. Such localized straining is possible by the method of the present invention detailed below.

More than one type of elastic layer 30 can be used with beneficial results. For example, a elastic layer 30 can be a three-dimensional formed film. Macroscopically-expanded, vacuum-formed, three-dimensional formed film, such as described in commonly-assigned U.S. Ser. No. 08/816,106, entitled "Tear Resistant Porous Extensible Web" filed by Curro et al. on Mar. 14, 1997, and hereby incorporated herein by reference. Further, the (or "a") elastic layer can be a three-dimensional formed film having micro-apertures such as described in commonly-assigned U.S. Pat. No. 4,629,643 issued to Curro et al. on Dec. 16, 1986, and U.S. Pat. No. 4,609,518, issued to Curro et al. on Sep. 2, 1986, both of which are hereby incorporated herein by reference.

The elastic layer can be a web material having a strainable network as disclosed in U.S. Pat. No. 5,518,801 issued to Chappell et al. on May 21, 1996, and hereby incorporated herein by reference. Such a web can be a structural elastic-like film (SELF) web, formed by, for example, embossing by mating plates or rolls.

The elastic layer 30 may comprise absorbent gelling materials. For example, supersorbers or hydrogel materials may provide for superior absorbency when the laminate web of the present invention is used as an absorbent wipe or an absorbent core in a disposable absorbent article. By "hydrogel" as used herein is meant an inorganic or organic compound capable of absorbing aqueous fluids and retaining them under moderate pressures. For good results the hydrogels should be water insoluble. Examples are inorganic materials such as silica gels and organic compounds such as cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinyl pyridine and the like.

One benefit of the laminate of the present invention is the ability to make an elastic laminate structure without the use of adhesive for joining. Because the elastic layer of the laminate web 10 is penetrated by the protuberances of the calendaring roll at melt bond sites, it can comprise non-thermally-bondable materials. For example, an additional central layer can be laminated between outer layers 20 and 40 (in addition to the elastic layer 30), which is non-thermally-bondable, such as absorbent layer, i.e. tissue or a superabsorbent. The plurality of melt bond sites 50 are sufficient to keep the component webs together in the laminate web, so that the laminate web behaves as a unitary web for processing integrity and use, without unwanted delamination. However, in some embodiments, and for certain materials, it may be beneficial to apply adhesive between at least two of the constituent layers.

The elastomeric laminate web of the present invention, being bonded by a plurality of relatively closely spaced thermal bond sites (without the use of thermoplastic adhesives) can be beneficially used for durable articles. For example, a laminate web of the present invention comprising nonwoven web outer layers and having a clothlike feel and appearance, can be used in durable garments. Certain embodiments of the laminate web of the present invention can survive repeated washing and drying in household washing and drying equipment, depending on the component webs of the laminate, and the level of thermal bonding. Due to the knit-like or fabric-like look and feel of certain embodiments of the present invention, such durability can result in durable articles such as drapes, upholstery, and garment components such as interliners and the like.

Method of Making

Figure 9:
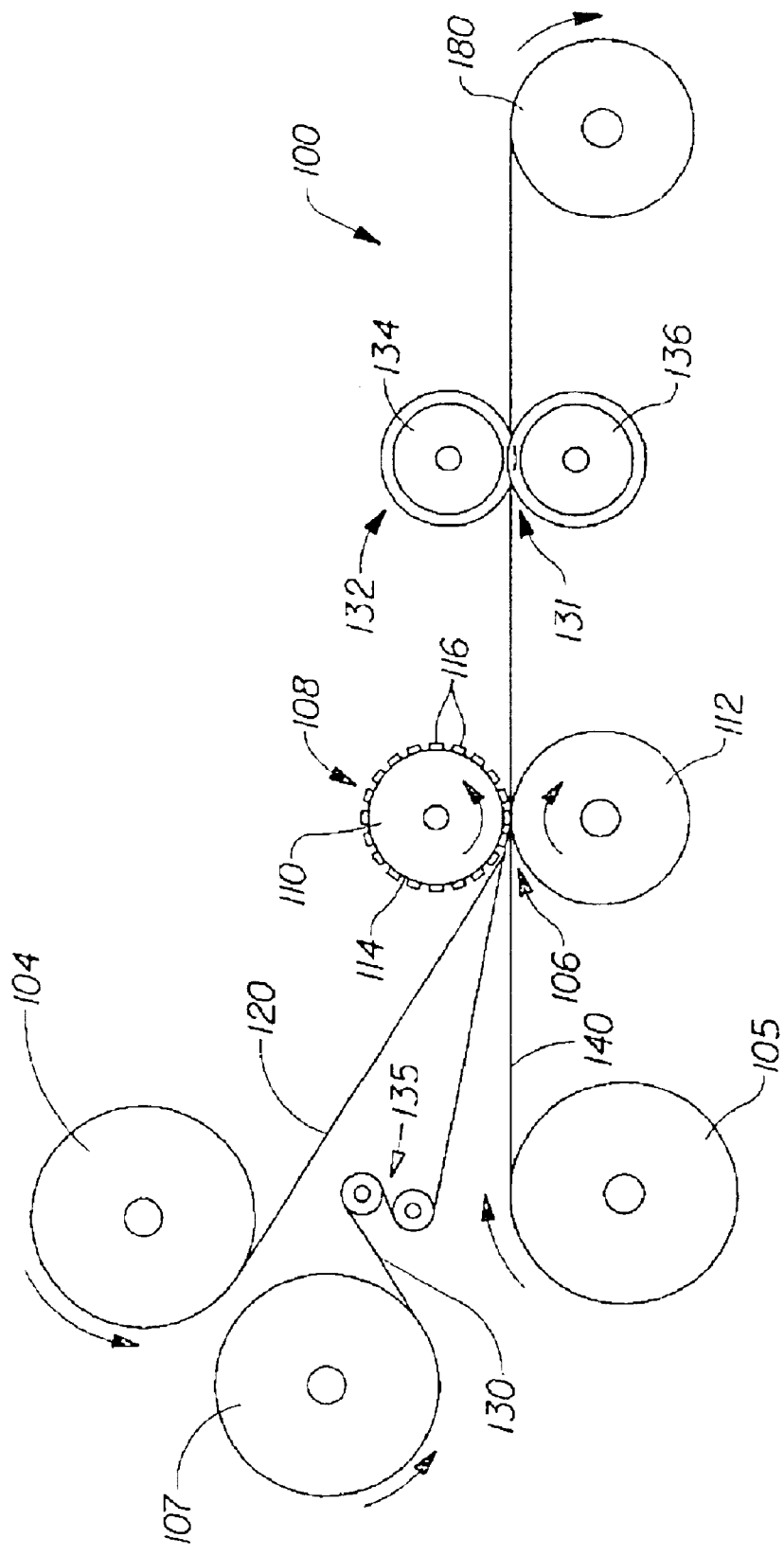
FIG. 9 is a schematic representation of a process for making a laminate web of the present invention.

Referring to FIG. 9 there is schematically illustrated at 100 a process making a laminate web of the present invention.

A first web 120 which can be a relatively extensible web, is unwound from a supply roll 104 and travels in a direction indicated by the arrows associated therewith as the supply roll 104 rotates in the direction indicated by the arrows associated therewith. Likewise a second web 140, which can be a relatively extensible web is unwound from supply roll 105. An elastic layer 130 is likewise drawn from supply roll 107. The three components (or more, if more than one central layer is used) pass through a nip 106 of the thermal point bond roller arrangement 108 formed by rollers 110 and 112.

Prior to passing through nip 106, elastic layer 130 is tensioned to a predetermined amount by the stacked S-wrap roller arrangement 135 as known in the art. S-wrap roller arrangement 135 retards the linear velocity of the web 130, which is consequently stretched by the pull of the remaining line components, such as bond roller arrangement 108, as described below. Any method known in the art can be used to achieve a stretched elastic layer 130. In general, it is desirable to achieve at least about 10% elongation or more, or about 50% to about 150% elongation for elastic layer 130 as it enters nip 106.

In one embodiment all constituent layers 120, 130, and 140 are of the same width, measured in the cross direction. However, in another embodiment, elastic layer 130 can be significantly less wide than either of the other two layers 120 or 140. In this embodiment, elastic layer 130 would result in a relatively narrow band or strip of elastic layer 30 in finished elastic web 10. In another embodiment a plurality of bands or strips of elastic layer 130 can be provided, resulting in an elastic web 10 having a plurality of elastic band layers 30.

In addition to thermoplastic nonwoven materials, either outer layer can comprise a polymeric film, for example a polyolefinic (e.g., PP or PE) thin film. If the entire outer layer is not uniformly thermoplastic, at least sufficient amounts to effect melt bonding must be thermoplastic. Conjugate fibers, such as bicomponent fibers can be used in the outer layers to facilitate thermal bonding of the outer layers. Either outer layer can comprise a formed film, such as a three-dimensional formed film having micro-apertures such as described in commonly-assigned U.S. Pat. No. 4,629,643 issued to Curro et al. on Dec. 16, 1986, and U.S. Pat. No. 4,609,518, issued to Curro et al. on Sep. 2, 1986, both of which are hereby incorporated herein by reference.

In a preferred embodiment, both outer layers comprise nonwoven materials, and may be the identical. The nonwoven material may be formed by known nonwoven extrusion processes, such as, for example, known meltblowing processes or known spunbonding processes, and passed directly through the nip 106 without first being bonded and/or stored on a supply roll. However, in a preferred embodiment, the nonwoven webs are themselves thermally point bonded (consolidated) webs commercially available on supply rolls. The thermal point bonds, which are typically in the form of a regular pattern of spaced-apart diamond shaped bond sites, are present in the nonwoven as purchased from a nonwoven vendor, and are to be distinguished in the web of the present invention from the bond sites 50 formed by the method of the present invention.

The nonwoven web outer layer(s) may be elastic, highly elastic or nonelastic. The nonwoven web may be any melt-fusible web, including a spunbonded web, a meltblown web, or a bonded carded web. If the nonwoven web is a web of meltblown fibers, it may include meltblown microfibers. The nonwoven web may be made of fiber forming polymers such as, for example, polyolefins. Exemplary polyolefins include one or more of polypropylene, polyethylene, ethylene copolymers, propylene copolymers, and butene copolymers.

The nonwoven web can have a basis weight between about 10 to about 100 grams per square meter (gsm), and more preferably about 15 to about 30 gsm.

The nonwoven web outer layers may themselves be a multilayer material having, for example, at least one layer of a spunbonded web joined to at least one layer of a meltblown web, a bonded carded web, or other suitable material.

The nonwoven web outer layers may also be a composite made up of a mixture of two or more different fibers or a mixture of fibers and particles. Such mixtures may be formed by adding fibers and/or particulates to the gas stream in which meltblown fibers or spunbond fibers are carried so that an intimate entangled co-mingling of fibers and other materials, e.g., wood pulp, staple fibers and particles occurs prior to collection of the fibers.

Figure 10:
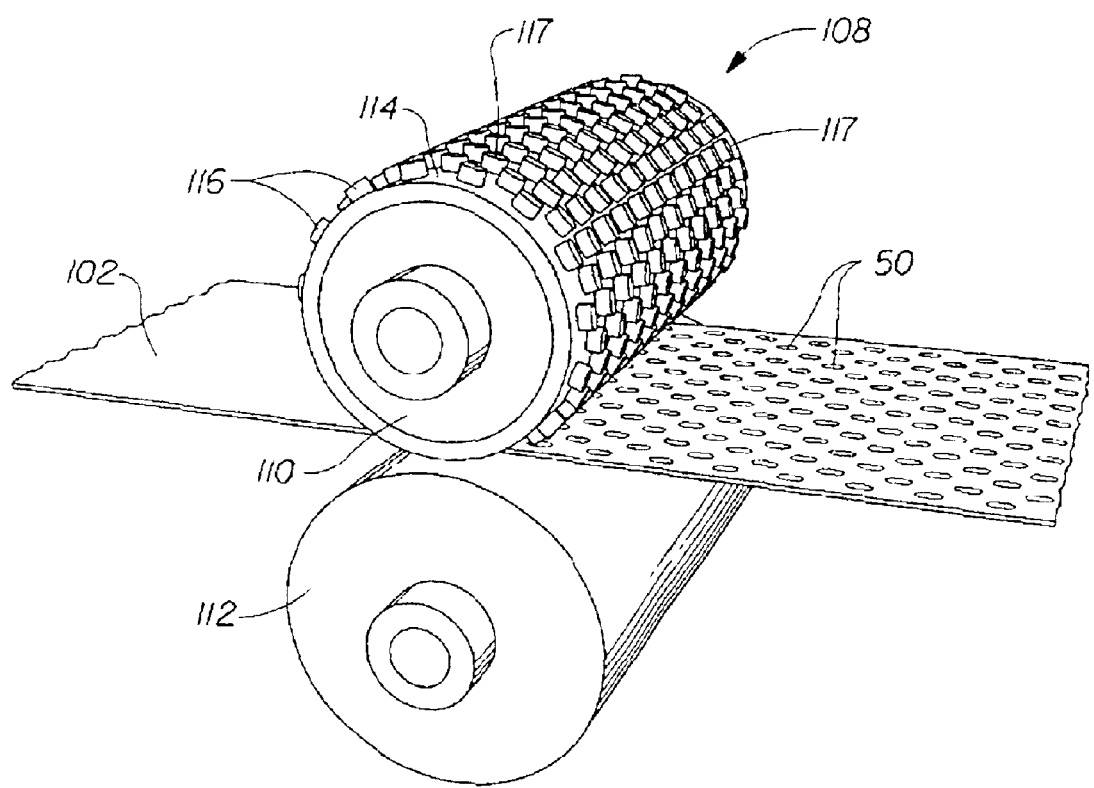
FIG. 10 is a perspective view of a melt bond calendaring apparatus.
Figure 11:
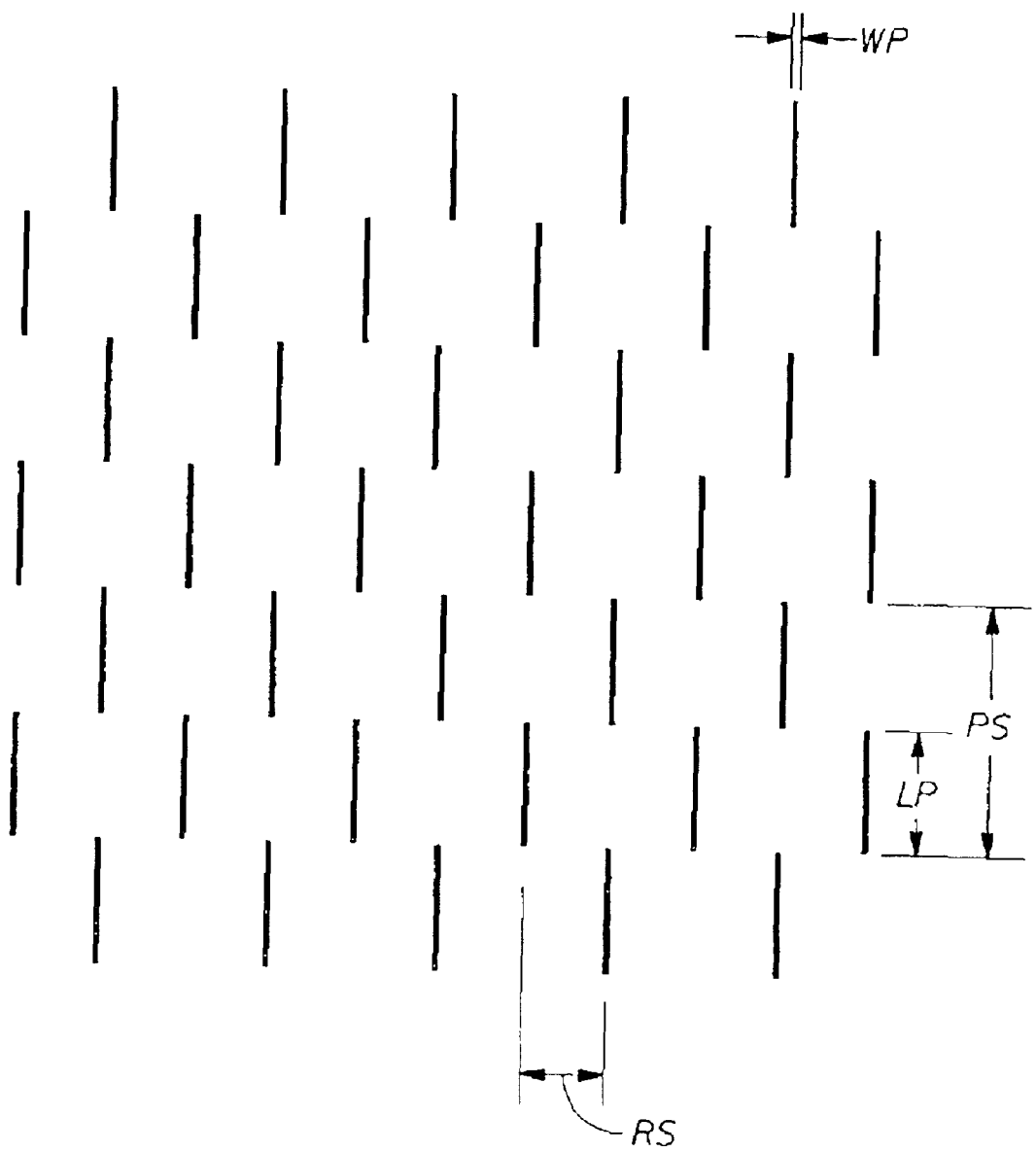
FIG. 11 is a schematic representation of a pattern for the protuberances of the calendaring roll.

Referring to FIGS. 9 and 10, the nonwoven thermal bond roller arrangement 108 preferably comprises a patterned calendar roller 110 and a smooth anvil roller 112. One or both of the patterned calendar roller 110 and the smooth anvil roller 112 may be heated and the temperature of either roller and the pressure between the two rollers may be adjusted by well known means to provide the desired temperature, if any, and pressure to concurrently displace elastic layer 130 at melt bond sites, and melt bond the two outer layers together at a plurality of bond sites.

The patterned calendar roller 110 is configured to have a circular cylindrical surface 114, and a plurality of protuberances or pattern elements 116 which extend outwardly from surface 114. The protuberances 116 are disposed in a predetermined pattern with each protuberance 116 being configured and disposed to displace elastic layer 30 at melt bond sites, and melt bond the two outer layers together at a plurality of locations. One pattern of protuberances is shown schematically in FIG. 11. As shown, the protuberances 116 have a relatively small width, WP, which can be between about 0.003 inches and 0.020 inches, but in a preferred embodiment is about 0.010 inches. Protuberances can have a length, LP, of between about 0.030 inches and about 0.200 inches, and in a preferred embodiment has a length of about 0.100 inches. In a preferred embodiment, the protuberances have an aspect ratio (LP/WP) of 10. The pattern shown is a regular repeating pattern of staggered protuberances, generally in rows, each separated by a row spacing, RS, of about between about 0.010 inches and about 0.200 inches. In a preferred embodiment, row spacing RS is about 0.060 inches. The protuberances can be spaced apart within a row by a protuberance spacing, PS generally equal to the protuberance length, LP. But the spacing and pattern can be varied in any way depending on the end product desired.

As shown in FIG. 10, patterned calendar roller 110 can have a repeating pattern of protuberances 116 which extend about the entire circumference of surface 114. Alternatively, the protuberances 116 may extend around a portion, or portions of the circumference of surface 114. Likewise, the protuberances 116 may be in a nonrepeating pattern, or in a repeating pattern of randomly oriented protuberances. Of course, if randomly oriented, the opening of the resulting bond sites into apertures will also be somewhat random, depending on the orientation of the bond site with respect to the direction of tension, as discussed below. For example, if the web is tensioned in the cross-direction (CD) direction only, then the bond sites 50 having a longitudinal axis 1 with a vector component in the machine direction (MD) will open into an aperture, at least to the degree of the magnitude of such a vector component.

The protuberances 116 are preferably truncated conical shapes which extend radially outwardly from surface 114 and which have rectangular or somewhat elliptical distal end surfaces 117. Although it is not intended to thereby limit the scope of the present invention to protuberances of only this configuration, it is currently believed that the high aspect ratio of the melt bond site 50 is only achievable if the protuberances likewise have a narrow width and a high aspect ratio at the distal end surfaces 117, as shown above with reference to FIG. 11. The roller 110 is preferably finished so that all of the end surfaces 117 lie in an imaginary right circular cylinder which is coaxial with respect to the axis of rotation of roller 110.

The height of the protuberances should be selected according to the thickness of the laminate being bonded. In general, the height dimension should be greater than the maximum thickness of the laminate web during the calendaring process, so that adequate bonding occurs at the bond sites, and only at the bond sites.

Anvil roller 112, is preferably a smooth surfaced, right circular cylinder of steel.

After passing through nip 106, the three (or more) component webs 120, 130, and 140, shown together as web 102 in FIG. 10, have been formed into laminate web 10 that is elastic in at least one direction. In particular, the unitary laminate web 10 is elastic in the machine direction MD.

At this point in the process the outer layers are thermally bonded to each other by the high aspect ratio bond sites 50 and unapertured, as shown in FIGS. 1 and 2. Elastic layer 30, from web 130, is apertured, having been displaced by protuberances 116 in nip 106. Depending on the elastic layer used, it may or may not participate in the bonding about the periphery of the bond sites. In some instances, particularly for non-thermoplastic, non-fibrous materials, elastic layer may not be involved in the bonding of the outer layers at all. However, for thermoplastic materials, and fibrous materials, some involvement of the elastic layer is observed.

Further, at this point in the process, if the elastic material 130 is elastic in the cross direction CD, the unitary laminate web 10 can be made elastic in the cross direction CD by extending the laminate web in the cross direction, which causes the apertures to form, as well as facilitating elastic extensibility. Such a web is not apertured, but can be apertured via tension in the cross direction, which tends to cause fracture of bond sites 50 that are then formed into apertures. This web is referred to herein a uni-directional elastomeric web, since it has elastomeric properties in the machine direction, even without being stretched in the cross direction to form apertures therein. Thus, the unitary laminate web 10 can be beneficially used in the unapertured condition exhibited at this point of the process as a unidirectional stretch material.

Although apertures can be formed in portions of web 10 simply by applying tension by any known method, including by hand, it is preferred to form apertures in the laminate web 10 in the whole laminate web by uniformly extending portions of the web in a direction orthogonal to the axis 1 of bond sites 50 (in the embodiments exhibited, the cross direction). As shown in FIGS. 9 and 10, the axis 1 is generally parallel to the machine direction MD of the web being processed. Therefore, extension in the cross-direction CD at the bonded portions causes the bond sites 50 to rupture and open to form apertures in the web.

One method for forming apertures across the web is to pass the web through nip 131 formed by an incremental stretching system 132 employing opposed pressure applicators 134 and 136 having three-dimensional surfaces which at least to a degree are complementary to one another. Stretching of the laminate web may be accomplished by other methods known in the art, including tentoring, or even by hand. However, to achieve even strain levels across the web, and especially if localized strain differential are desired, the incremental stretching system disclosed herein is preferred.

Figure 12:
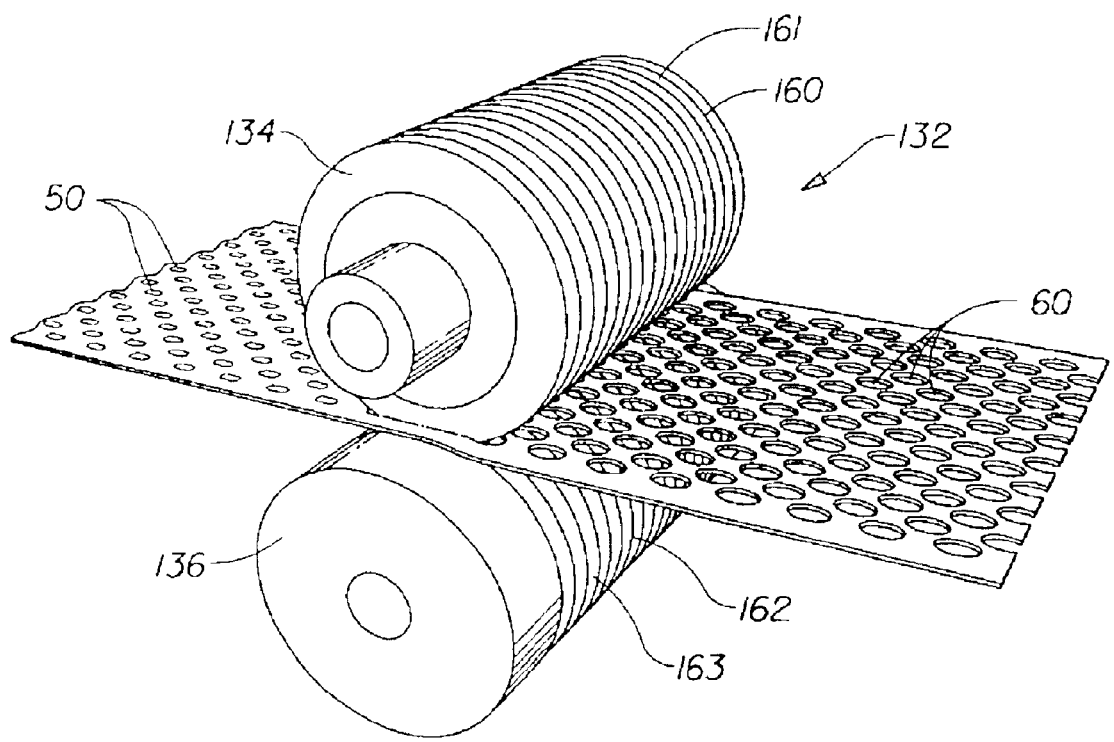
FIG. 12 is a perspective view of an apparatus for stretching a laminate of the present invention to form apertures therein.
Figure 13:
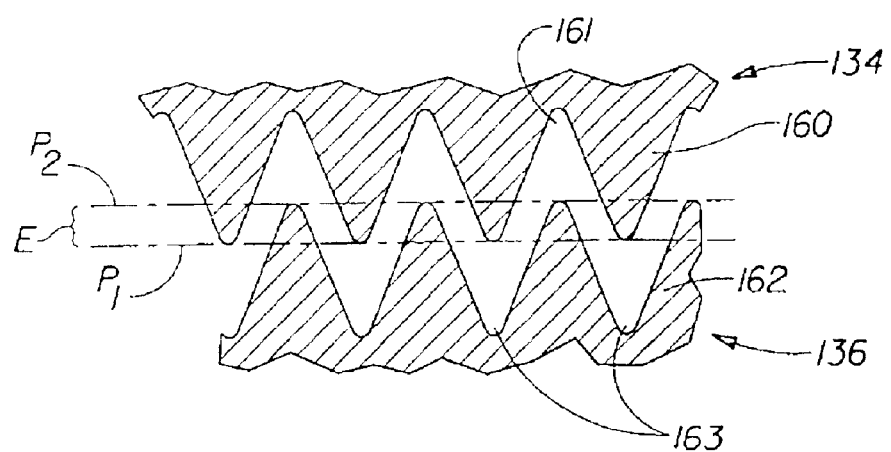
FIG. 13 is a cross-sectional view of a portion of the mating portions of the apparatus shown in FIG. 12.

Referring now to FIG. 12, there is shown a fragmentary enlarged view of the incremental stretching system 132 comprising incremental stretching rollers 134 and 136. The incremental stretching roller 134 includes a plurality of teeth 160 and corresponding grooves 161 which extend about the entire circumference of roller 134. Incremental stretching roller 136 includes a plurality of teeth 162 and a plurality of corresponding grooves 163. The teeth 160 on roller 134 intermesh with or engage the grooves 163 on roller 136, while the teeth 162 on roller 136 intermesh with or engage the grooves 161 on roller 134. The teeth of each roller are generally triangular-shaped, as shown in FIG. 13. The apex of the teeth may be slightly rounded, if desired for certain effects in the finished web.

FIG. 13 shows a portion of the intermeshing of the teeth 160 and 162 of rollers 134 and 136, respectively. The term "pitch" as used herein, refers to the distance between the apexes of adjacent teeth. The pitch can be between about 0.02 to about 0.30 inches, and is preferably between about 0.05 and about 0.15 inches. The height (or depth) of the teeth is measured from the base of the tooth to the apex of the tooth, and is preferably equal for all teeth. The height of the teeth can be between about 0.10 inches and 0.90 inches, and is preferably about 0.25 inches and 0.50 inches.

The teeth 160 in one roll can be offset by one-half the pitch from the teeth 162 in the other roll, such that the teeth of one roll (e.g., teeth 160) mesh in the valley (e.g., valley 163) between teeth in the mating roll. The offset permits intermeshing of the two rollers when the rollers are "engaged" or in an intermeshing, operative position relative to one another. In a preferred embodiment, the teeth of the respective rollers are only partially intermeshing. The degree to which the teeth on the opposing rolls intermesh is referred to herein as the "depth of engagement" or "DOE" of the teeth. As shown in FIG. 13, the DOE, E, is the distance between a position designated by plane P1 where the apexes of the teeth on the respective rolls are in the same plane (0% engagement) to a position designated by plane P2 where the apexes of the teeth of one roll extend inward beyond the plane P1 toward the valley on the opposing roll. The optimum or effective DOE for particular laminate webs is dependent upon the height and the pitch of the teeth and the materials of the web.

In other embodiments the teeth of the mating rolls need not be aligned with the valleys of the opposing rolls. That is, the teeth may be out of phase with the valleys to some degree, ranging from slightly offset to greatly offset.

As the laminate web 10 having melt bonded locations 50 passes through the incremental stretching system 132 the laminate web 10 can be subjected to tensioning in the CD or cross-machine direction causing the laminate web 10 to be extended in the CD direction. Alternatively, or additionally, the laminate web 10 may be tensioned in the MD (machine direction). The tensioning force placed on the laminate web 10 can be adjusted (e.g., by adjusting DOE) such that it causes the melt bonded locations 50 to separate or rupture creating a plurality of apertures 60 coincident with the melt bonded locations 50 in the laminate web 10. However, portions of the melt bonds of the laminate web 10 remain, as indicated by portions 62 in FIG. 4, thereby maintaining the laminate web in a coherent, unitary web condition even after the melt bonded locations rupture.

After being subjected to the tensioning force applied by the incremental stretching system 132, the laminate web 10 includes a plurality of apertures 60 which are coincident with the melt bonded regions 50 of the laminate web. As mentioned, a portion of the circumferential edges of apertures 60 include remnants 62 of the melt bonded locations 60. It is believed that the remnants 60 help to resist further tearing or delamination of the laminate web. Remnants 62 may also contain portions of elastic layer 30, to the extent that the elastic layer is involved in the bonding.

Figure 14:
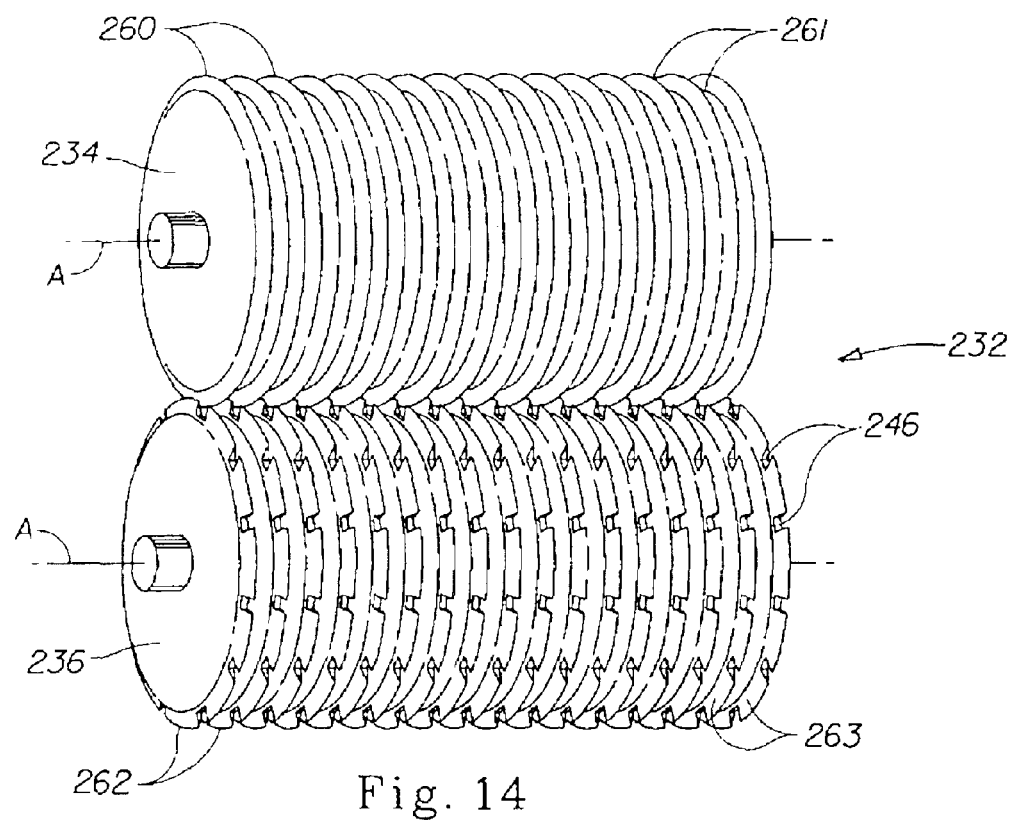
FIG. 14 is a perspective view of an alternative apparatus for stretching a laminate of the present invention in the cross-machine direction to form apertures therein.

Instead of two substantially identical rolls 134 and 136, one or both rolls can be modified to produce extension and additional patterning. For example, one or both rolls can be modified to have cut into the teeth several evenly-spaced thin channels 246 on the surface of the roll, as shown on roll 236 in FIG. 14. In FIG. 14 there is shown an enlarged view of an alternative incremental stretching system 232 comprising incremental stretching rollers 234 and 236. The incremental stretching roller 234 includes a plurality of teeth 260 and corresponding grooves 261 which extend about the entire circumference of roller 234. Incremental stretching roller 236 includes a plurality of teeth 262 and a plurality of corresponding grooves 263. The teeth 260 on roller 234 intermesh with or engage the grooves 263 on roller 236, while the teeth 262 on roller 236 intermesh with or engage the grooves 261 on roller 234. The teeth on one or both rollers can have channels 246 formed, such as by machining, such that regions of undeformed laminate web material may remain after stretching. A suitable pattern roll is described in U.S. Pat. No. 5,518,801, issued May 21, 1996, in the name of Chappell, et al., the disclosure of which is incorporated herein by reference.

Figure 15:
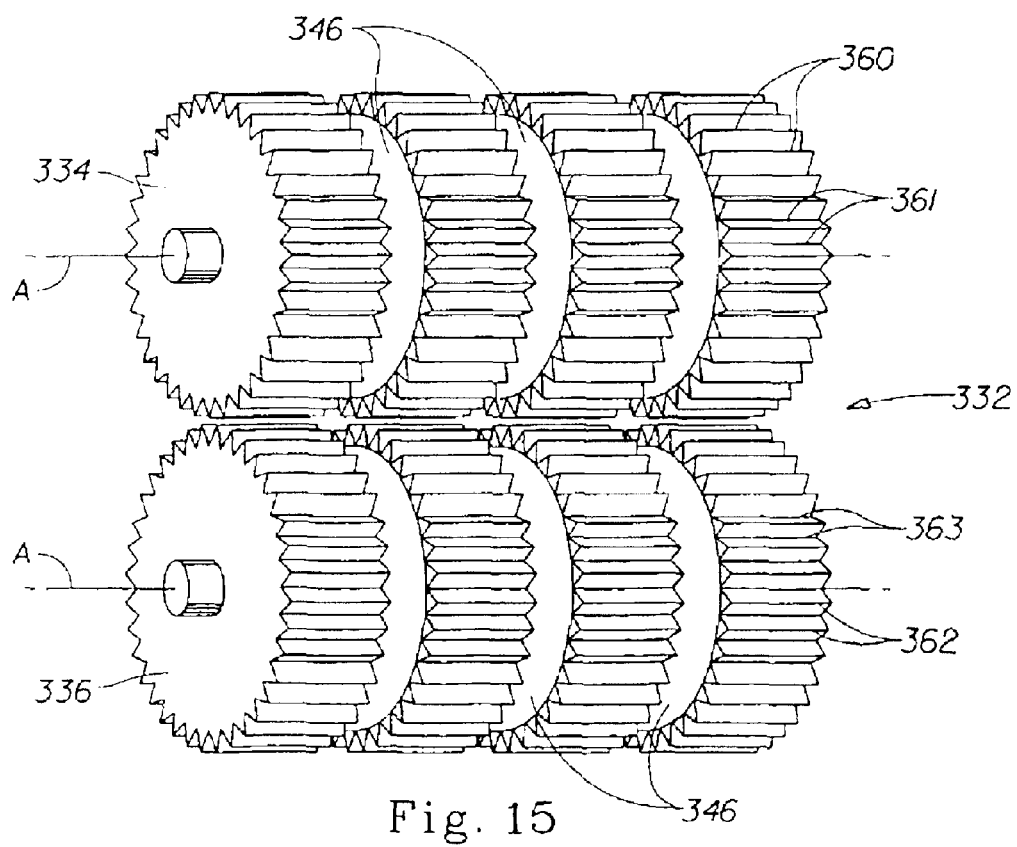
FIG. 15 is a perspective view of another alternative apparatus for stretching a laminate of the present invention in the machine direction to form apertures therein.

In certain embodiment wherein the axis 1 of bond sites 50 is oriented generally parallel to the cross-machine, CD direction, the incremental stretching can be achieved by use of mating rolls oriented as shown in FIG. 15. Such rolls comprise a series of ridges 360, 362, and valleys, 361, 363 that run parallel to the axis, A, of the roll, either 334 or 336, respectively. The ridges form a plurality of triangular-shaped teeth on the surface of the roll. Either or both rolls may also have a series of spaced-apart channels 346 that are oriented around the circumference of the cylindrical roll. Rolls as shown are effective in incrementally stretching a laminate web 10 in the machine direction, MD if the axis 1 of bond sites 50 is oriented generally parallel to the cross-machine, CD direction of the web as its being processed.

Figure 16:
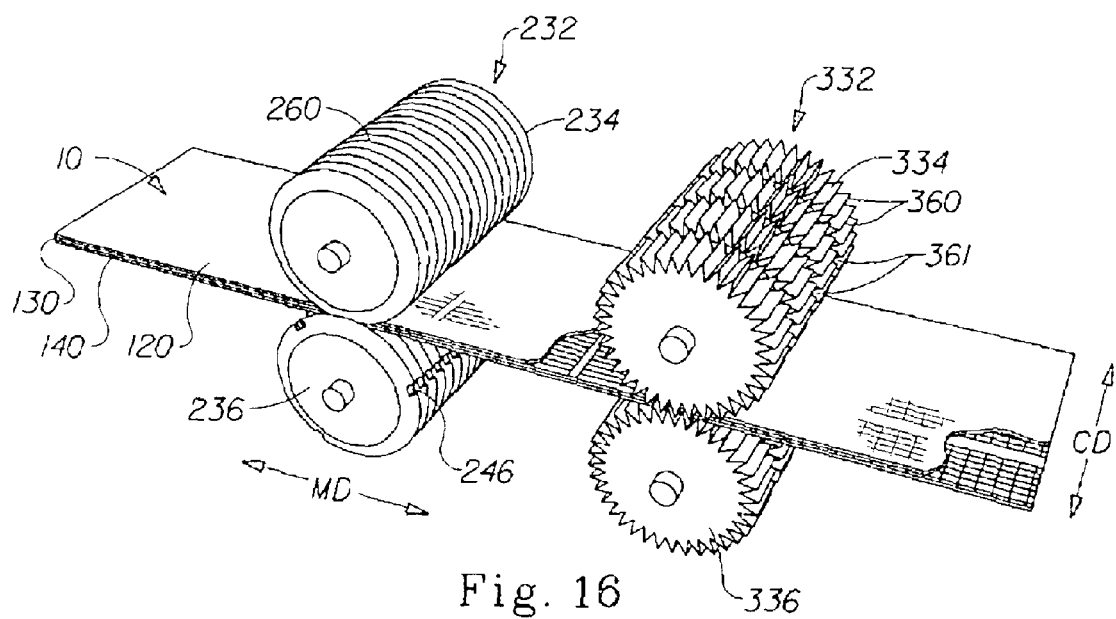
FIG. 16 is a perspective representation of an apparatus for stretching a laminate of the present invention in both the cross-machine and machine directions to form apertures therein.

In one embodiment, the method of the present invention can comprise both CD and MD incremental stretching. This method is particularly useful if bond sites 50 are oriented in two or more directions, such as in a herringbone pattern. As shown in FIG. 16, two pairs of incremental stretching rolls can be used in line, such that one pair (232, which, as shown in FIG. 16 includes a series of spaced-apart channels 246) performs CD stretching, and another pair, 332 performs MD stretching. By this method many interesting fabric-like textures can be made. The resulting hand and visual appearance make such fabric-like webs ideal for use in elastic articles benefiting from a fabric-like look and feel.

The elastic laminate webs of the present invention may be utilized in many varied applications. For example, the relatively low cost of nonwoven and film materials makes the laminates ideally suited for disposable articles, such as disposable diapers. The elastic laminate web can be used for the elastic waist or side panel portion of such diapers, for example. A preferred diaper configuration for a diaper in which elastic laminates of the present invention can be used as elastic waist or side panel portions is described generally in U.S. Pat. No. 3,860,003, issued Jan. 14, 1975 to Buell. Alternatively preferred configurations for disposable diapers are also disclosed in U.S. Pat. No. 4,808,178 (Aziz et al.); U.S. Pat. No. 4,695,278 (Lawson); U.S. Pat. No. 4,816,025 (Foreman); U.S. Pat. No. 5,151,092 (Buell et al.), all of which are hereby incorporated herein by reference.

In addition to disposable diapers, various embodiments of elastic laminates of the present invention are useful for use in other disposable absorbent articles, such as catamenials, panty liners, pull-up diapers, adult incontinence products, and the like.

The elastic web of the present invention is also useful for use as stretch fitting upholstery and furniture covers. The beneficial soft, fabric-like look and feel, together with elastomeric properties, makes the web of the present invention a low cost, semidurable alternative to knits and woven products. In one embodiment, a mattress cover comprises a unidirectional stretch elastic laminate. The elastic laminate web 10 of the invention can be sewed onto a mattress cover in such a manner so as to provide elastic tensioning at the corners, or about the entire periphery of the mattress. In one embodiment, the entire mattress cover can consist of an elastic laminate web 10 of the present invention.

Other uses for laminates of the present invention include medical dressings; articles of apparel, such as medical gowns and garment sleeve cuffs; bandages, textured wall coverings, and the like. In general, any application of elastics in apparel, durable garments, disposable articles, furniture coverings, sports equipment, and the like are possible applications of elastic laminate webs of the present invention.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. A laminate web having a plurality of apertures, said laminate web comprising:
   a) first and second extensible webs being joined at a plurality of discrete bond sites having an aspect ratio of greater than about 3;
   b) a non-thermoplastic elastic material disposed between said first and second nonwoven webs; and
   c) the first and second extensible webs being in fluid communication via the apertures.

2. The laminate web of claim 1, wherein said laminate is joined by bonds in the absence of adhesive.

3. The laminate web of claim 1, wherein said bond sites are discrete thermal bonds having an aspect ratio of at least about 10.

4. The laminate web of claim 1, wherein said first or second extensible web comprises a nonwoven.

5. The laminate web of claim 1 wherein said bond site has a width of less than about 0.020 inches.

6. A disposable absorbent article comprising an elastic laminate web having a plurality of apertures, said elastic laminate web comprising:
   a) a first web;
   b) a second web joined to said first web in a face to face relationship at a plurality of discrete bond sites having an aspect ratio of at least about 3, the first and second webs forming an interior region therebetween;
   c) a non-thermoplastic elastic material being disposed between at least a portion of said first and second webs; and d) said elastic material being apertured in regions coincident said bond sites, such that said first and second webs are joined through said apertures.

7. The disposable absorbent article of claim 6, wherein said first or second extensible web comprises a nonwoven.

8. The disposable absorbent article of claim 6, wherein said elastic laminate web further comprises absorbent gelling material.

9. The disposable absorbent article of claim 6 wherein said bond site has a width of less than about 0.020 inches.

10. An article of apparel comprising an elastic laminate web having a plurality of apertures, said article comprising:

a) a first web having a melting point;

b) a second web having a melting point joined to said first web in a face to face relationship at a plurality of discrete bond sites having an aspect ratio of at least about 3, the first and second webs forming an interior region therebetween;

c) an elastic material having a melting point higher than said melting points of said first and second webs and being more elastic than said first and second webs, wherein said elastic material is disposed between at least a portion of said first and second webs; and d) said elastic material being apertured in regions coincident said bond sites, such that said first and second webs are joined through said apertures.

11. The article of apparel of claim 10, wherein said first or second extensible web comprises a nonwoven.

12. The article of apparel of claim 10 wherein said bond site has a width of less than about 0.020 inches.

* * * * *